United States Patent [19]
Imran et al.

[11] Patent Number: 5,658,278
[45] Date of Patent: *Aug. 19, 1997

[54] CATHETER FOR RF ABLATION WITH COOLED ELECTRODE AND METHOD

[75] Inventors: Mir A. Imran, Palo Alto; Mark L. Pomeranz, Los Gatos, both of Calif.

[73] Assignee: Cardiac Pathways, Inc., Sunnyvale, Calif.

[*] Notice: The term of this patent shall not extend beyond the expiration date of Pat. No. 5,423,811.

[21] Appl. No.: 381,198

[22] Filed: Jan. 31, 1995

Related U.S. Application Data

[60] Continuation of Ser. No. 214,785, Mar. 16, 1994, Pat. No. 5,423,811, which is a division of Ser. No. 983,732, Dec. 1, 1992, Pat. No. 5,348,554.

[51] Int. Cl.[6] .............................. A61B 17/39; A61N 1/05
[52] U.S. Cl. .............................. 606/41; 607/99; 607/105; 607/113; 607/122
[58] Field of Search .............................. 607/98, 99, 101, 607/102, 104, 105, 113, 116, 122; 606/41, 45, 49

[56] References Cited

U.S. PATENT DOCUMENTS

| 4,907,589 | 3/1990 | Cosman | 606/41 |
| 5,230,349 | 7/1993 | Langberg | 607/122 |
| 5,281,213 | 1/1994 | Milder | 606/15 |
| 5,334,193 | 8/1994 | Nardella | 606/41 |
| 5,423,811 | 6/1995 | Imren et al. | 606/41 |

FOREIGN PATENT DOCUMENTS 1690786  11/1991  U.S.S.R. .............................. 606/41

OTHER PUBLICATIONS

Wittkampf et al, "Radiofrequency Ablation . . . Catheter", JACC, vol. 11, No. 2, Feb. 1988: 17A Abstracts.

Huang, et al. "Increase in the lesion size and decrease in the impedance rise with a saline infusion electrode catheter for radiofrequency catheter ablation" (Circulation, vol. 80, No. 4, Oct. 1989, Supplement II.

Borggrefe, et al., "High frequency alternating current ablation of an accessory pathway in humans" (JACC, vol. 10, No. 3, Sep. 1987:576–82).

Primary Examiner—Lee S. Cohen
Attorney, Agent, or Firm—Flehr Hohbach Test Albritton & Herbert LLP

[57] ABSTRACT

A catheter for radio frequency ablation with a cooled electrode for use in tissue having a surface comprising an elongate member having proximal and distal extremities. A metal conducting electrode secured to the distal extremity of the elongate member and having a chamber therein. A conductor extends through the elongate member from the proximal to the distal extremity for supplying radio frequency energy to the electrode. The elongate member has a lumen in the distal extremity which is in communication with the chamber. A coolant is disposed in the chamber and in contact with the electrode for dissipating heat created in the electrode by the application of radio frequency energy thereto.

7 Claims, 6 Drawing Sheets

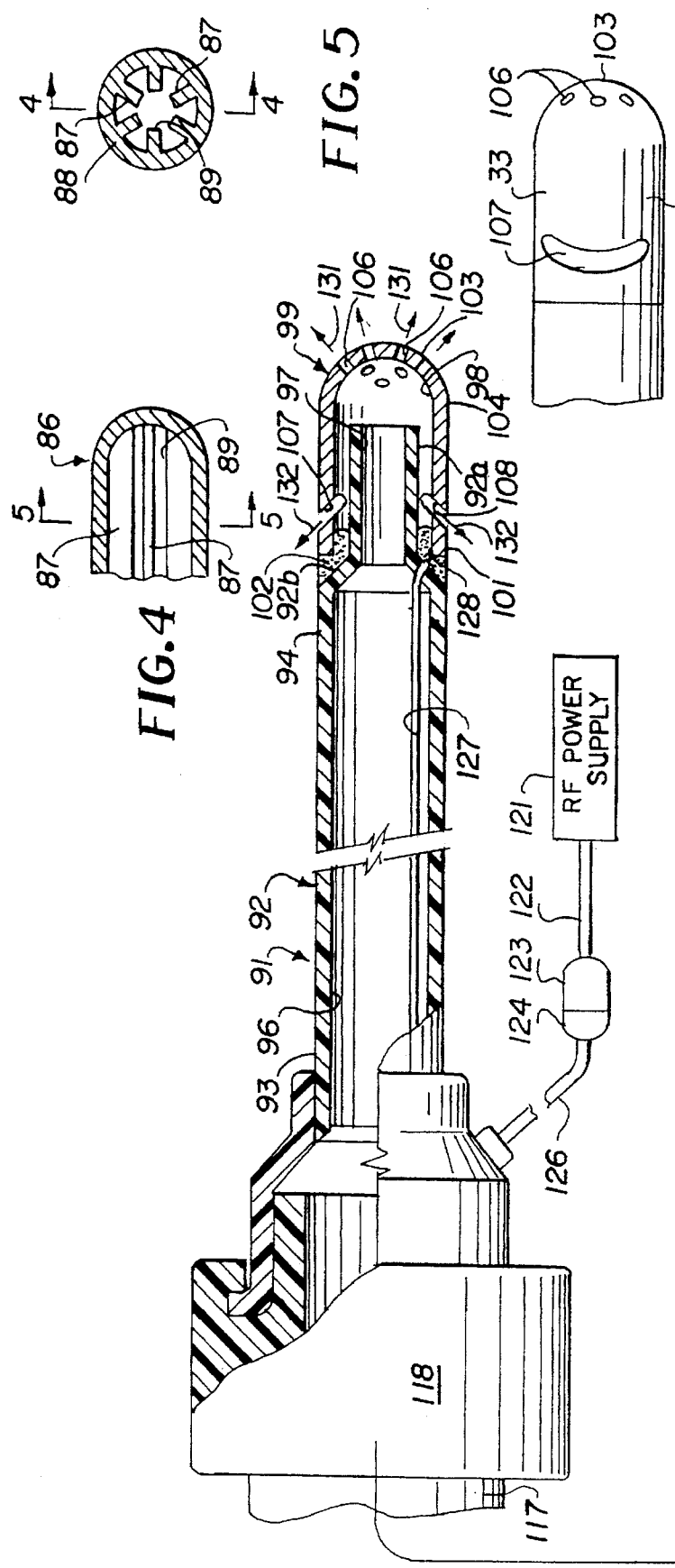

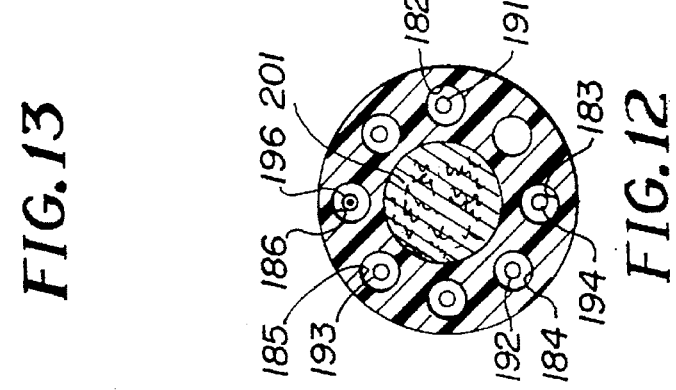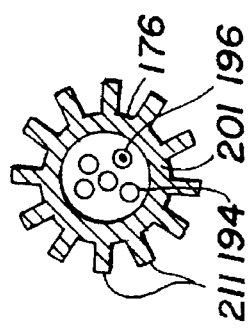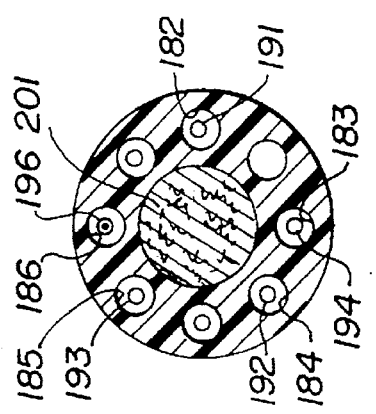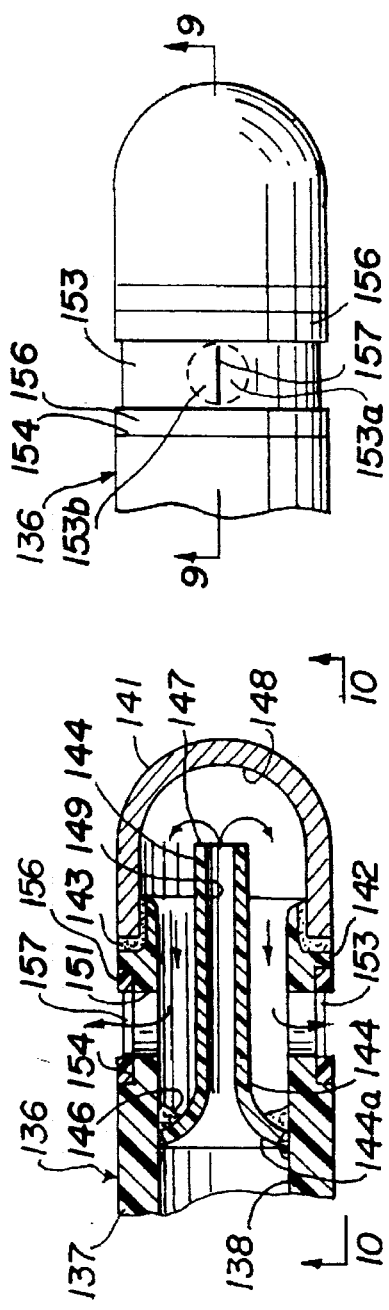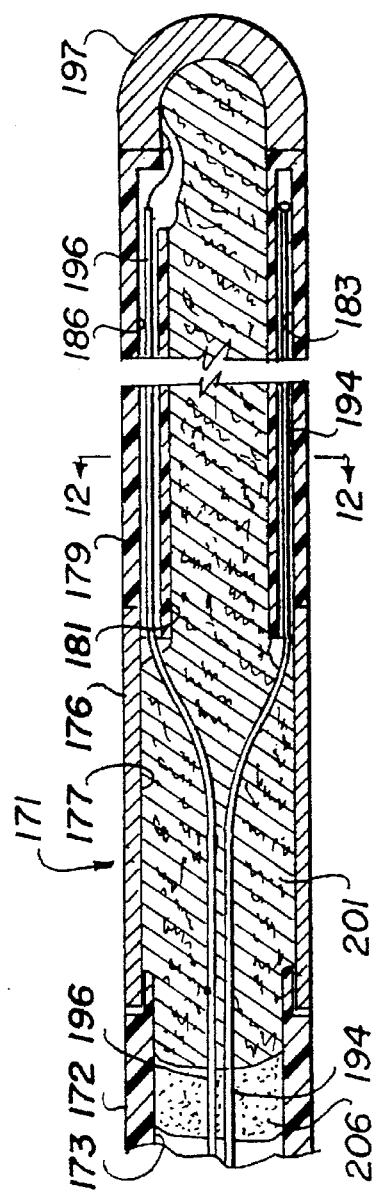

CATHETER FOR RF ABLATION WITH COOLED ELECTRODE AND METHOD

This is a continuation of application Ser. No. 08/214,785 filed Mar. 16, 1994 now U.S Pat. No. 5,423,811, which is division of application Ser. No. 07/983,732 filed Dec. 1, 1992, now U.S. Pat. No. 5,348,554.

BACKGROUND OF THE INVENTION

This invention relates to a catheter for radio frequency (RF) ablation which is provided with a cooled electrode and method.

Catheters for RF ablation have heretofore been provided. However, difficulties have been encountered with such catheters in that it has been difficult to achieve lesions of sufficient size. Increasing the RF power to the catheter in an attempt to increase the size of the lesions has caused degradation of the blood in the region where ablation is taking place. Such blood degradation has caused products of the degradation to be deposited on the electrode surface greatly increasing the impedance. In addition, it has been found that increased power levels create undesirable heating of the blood which can create blood clots. There is, therefore, a need for a new and improved catheter for RF ablation which overcomes these disadvantages.

SUMMARY OF THE INVENTION

In general, it is an object of the present invention to provide a catheter for RF ablation which is provided with a cooled electrode and a method to make possible the formation of large lesions.

Another object of the invention is to provide a catheter and method of the above character in which the catheter is provided with a conducting electrode having a chamber therein and in which a cooling is provided in the chamber.

Another object of the invention is to provide a catheter and a method of the above character in which the cooling liquid in the cavity is maintained at a pressure which is substantially equal to the pressure of the blood of the chamber in the heart in which the catheter is disclosed.

Another object of the invention is to provide a catheter and a method of the above character in which a pump is provided for introducing the cooling liquid into the catheter and a separate pump is provided for withdrawing the liquid from the catheter.

Another object of the invention is to provide a catheter and method by which lesions or a necrosis can be formed at various depths underlying the electrode with destroying the surface contacted by the electrode.

Additional objects and features of the invention will appear from the following description in which the preferred embodiment is set forth in detail in conjunction with the accompanying drawing.

BRIEF DESCRIPTION OF THE DRAWINGS

FIG. 4 is a cross-sectional view taken along the line 4—4 of FIG. 5 showing another embodiment of a cooled tip incorporating the present invention.

FIG. 5 is a cross-sectional view taken along the line 5—5 of FIG. 4.

FIG. 6 is a side elevational view of another embodiment of a catheter for use in radio frequency ablation with a cooled electrode incorporating the present invention showing the same schematically connected to a pumping system for supplying a cooling liquid to the tip of the catheter.

FIG. 7 is a partial side elevational view of the distal extremity of the catheter shown in FIG. 6.

FIG. 8 is a side elevational view similar to FIG. 7 but showing how the tip rotated through 90°.

FIG. 9. is a side elevational view in cross-sectional of another embodiment of a catheter incorporating the present invention taken along the line 9—9 of FIG. 10.

FIG. 10 is an end elevational view looking along the line 10—10 of FIG. 9.

FIG. 11 is another embodiment of a catheter incorporating the present invention utilizing a passive wick for withdrawing energy from the tip electrode of the catheter.

FIG. 12 is a cross-sectional view taken along the line 12—12 of FIG. 11.

FIG. 13 is a cross-sectional view of the distal extremity with another catheter incorporating the present invention.

DESCRIPTION OF THE PREFERRED EMBODIMENTS

In general, the present invention embodies a catheter for radio frequency ablation with a cooled electrode for use in a heart having a wall forming at least one chamber with blood therein. The catheter is comprised of a flexible elongate member having proximal and distal extremities. An electrode is mounted on the distal extremity of the flexible elongate member and has a cavity therein. Means is provided which extends through the flexible elongate member from the proximal to the distal extremity for supplying radio frequency energy to the tip electrode. The flexible elongate member is provided with a first lumen therein extending from the proximal extremity to the distal extremity and being in communication with the electrode. Means is provided for introducing a cooling liquid into the lumen. The means for introducing the cooling liquid into the lumen includes means for adjusting the pressure of the liquid in the lumen at the electrode so that it approximates the pressure of the blood in the chamber of the heart in which the distal extremity is disposed.

Figure 1:
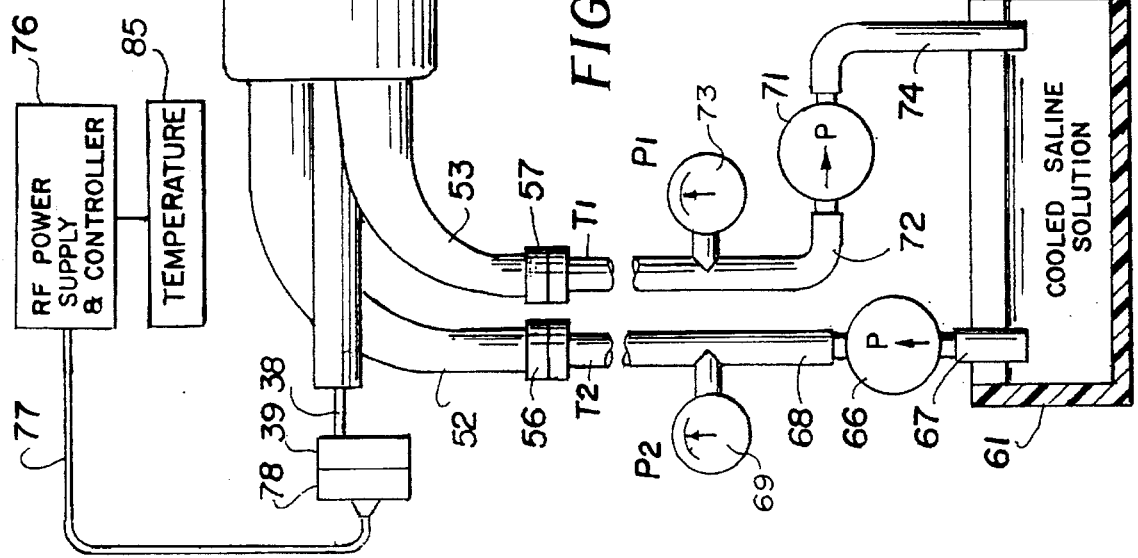
FIG. 1 is a side elevational view of a catheter for use in radio frequency ablation with a cooled electrode incorporating the present invention and showing the same being schematically connected to a pumping system for supplying and withdrawing cooling liquid from the tip of the catheter.

More in particular, the catheter 11 for RF ablation with a cooled electrode incorporating the present invention consists of a flexible elongate member 12 having proximal and distal extremities 13 and 14. A hollow tip conducting electrode 16 is mounted on the distal extremity 14 and is provided with an internal cavity 17. The flexibly elongate member 12 is formed of a suitable plastic such as a polyurethane. It is desirable that the plastic utilized be kink-resistant. In order to provide additional kink-resistance, braid 21 of a suitable material may be provided within the flexible elongate member 12 during extrusion of the same to reinforce the elongate member and to provide additional kink-resistance. The braid 21 can be formed of a suitable material such as Nylon or Kevlar. The braid 21 can be provided at the distal extremity of the elongate member as shown in FIG. 1 or, if desired, can extend the entire length of the elongate member 12.

The hollow tip electrode 16 can be formed of a suitable material such as stainless steel and can have a wall thickness ranging from 0.003 to 0.004 inches. The elongate member 12 can be provided in suitable sizes as, for example, to provide catheters from 3 to 7 French in size. The electrode 16 has a generally hemispherical configuration and can be secured to the distal extremity of the elongate member 12 by suitable means such as an adhesive (not shown). The elongate member 12 is provided with first and second relatively large liquid carrying lumens 26 and 27 which extend from the proximal extremity 13 to the distal extremity 14 and are in communication with the cavity 17 of the hollow tip electrode 16. As shown, lumens 26 and 27 can be crescent-shaped in cross-section. A central lumen 28 is also provided which extends from the proximal extremity 13 to the distal extremity 14 of the elongate member 12. A plurality of additional lumens 29 are provided which are spaced circumferentially around the crescent-shaped lumens 26 and 27. The central lumen 28 carries a conductor 31 for supplying radio frequency energy to the electrode 16. The conductor 31 also serves to secure the tip electrode 16 so that it remains secured to the distal extremity 14 of the elongate member 12.

Means is provided for steering the distal extremity of the catheter 11 and is of the type described in co-pending application, Ser. No. 07/793,858, filed Nov. 18, 1991, now U.S. Pat. No. 5,238,005. As described therein, it includes steering wires 33, 34 and 36 which are provided in the lumens 29 and which are spaced-apart circumferentially around the central lumen 28 of the elongate member 12. The steering wires 33, 34 and 36 together with the ground return 37 extend to the proximal extremity and are connected to a male connector 41 which is provided at the proximal extremity of the elongate member 12.

As shown, the catheter 11 can be provided with additional radio frequency electrodes as, for example, electrodes 41 and 42 which are formed as spaced-apart bands provided on the exterior of the distal extremity 14 of the elongate member 12 and in relatively close proximity to the hollow tip electrode 16. Such electrodes 41 and 42 can be connected by conductors 43 and 44 extending through lumens 29 to the proximal extremity and connected into the connector 41.

The proximal extremity 13 of the elongate member 12 is provided with a fitting 51 into which a tubular member 52 and which another tubular member 53 extends. Tubular member 52 is in communication with the lumen 27 and the tubular member 53 is in communication with the lumen 28. The tubular members 52 and 53 are provided with Luer locks 56 and 57 of a conventional type.

Means is connected to the fitting 56 for introducing a cooling liquid into the lumen 27 to cause the same to pass through the lumen to the distal extremity into the cavity 17. Means is secured to the fitting 57 for withdrawing the cooling liquid from the cavity 17 so that the pressure of the liquid in the cavity 17 approximates the pressure of the blood in the chamber of the heart in which a catheter is disposed. This means consists of a tank 61 which is provided with a cooled saline solution 62 therein having a temperature ranging from 5° to 10° Centigrade. It should be appreciated other liquids other than a saline solution can be utilized, if desired. The means provided for supplying the saline cooling solution to the fitting 56 consists of a pump 66 which is connected by a tubular member 67 into the saline cooling solution 62 in the tank 61 and delivers the same through tubular member 68 which is connected to the fitting 56 to provide the cooled saline solution at a predetermined pressure P1 as measured by the pressure gauge 69. Thus, as the pump 66 is operated, the cooled saline solution is introduced into the lumen 27 and into the cavity 17. In order to reduce the pressure of the cooled liquid in the cavity 17 and to maintain the pressure in the cavity 17 so that it is substantially equal to the pressure of the blood in the chamber of the heart in which the catheter is disposed, a pump 71 is provided for withdrawing the cooled liquid from the cavity 17 through the lumen 28. The pump 71 is connected by a tubular member 72 to the fitting 57 and supplies a negative pressure P2 to the flow passage 28 which is measured by the pressure gauge 73. The pump 71 returns the cooled liquid withdrawn from the cavity 17 through a tubular member 74 into the tank 61 so that it can be cooled and reused.

The catheter 11 is adapted to be connected to radio frequency power supply and controller 76 which is connected by cable 77 to a female connector 78 which is adapted to receive the male connector 32. The radio frequency power supply 76 can be of a conventional type. The controller incorporates as a part thereof apparatus which is utilized for steering the distal extremity of the catheter, of the type described in co-pending application, Ser. No. 07/793,858, filed Nov. 18, 1991 now U.S. Pat. No. 5,238, 005.

Operation and use of the catheter for RF ablation with the cooled tip and the method for using the same can now be briefly described as follows. Let it be assumed that it is desired to introduce radio frequency energy into the wall forming a chamber of the heart to cause ablation of the myocardium. Also let it be assumed that the catheter is introduced into the chamber of a heart in a human being in a conventional manner. By utilizing the controller 76, the distal extremity 14 is steered so that the tip electrode 16 is moved into contact with the myocardium. The high frequency energy can then be supplied from the RF power supply 76 to the tip 16 through the conductor 31. Prior to the delivery of such radio frequency energy or at the same time, the pumps 66 and 71 are placed in operation so that a cooled saline solution is being introduced into the lumen 27 and into the cavity 17 of the electrode 16 to cool the electrode 16 during the time that radio frequency energy is being applied to the same. In order to keep the pressure in the lumen 27 at a relatively low value and so that the pressure in the cavity 17 is substantially the same as the pressure of the blood in the chamber of the heart in which the catheter is disposed, the pump 73 creates a negative pressure to withdraw the cooled saline solution through the passage or lumen 28 and discharges the same into the tank 61. The operator by observing the gauges 69 and 73 can operate the pumps 66 and 71 in a such a manner so that the pressure in the cavity 17 is substantially the same as the pressure of the blood pool surrounding the cavity in which the catheter tip is disposed. The desired pressures P1 and P2 on the gauges 69 and 73 can be ascertained by first operating the pumps 66 and 71 with the catheter 11 outside of the body and measuring the pressure in the chamber 17 and then observing the pressures on the gauges 69 and 73 when the proper pressure is present in the cavity 17. Thus, when the catheter 11 is introduced into the body and into the heart, the desired pressure in the cavity 17 can be achieved merely by duplicating the readings on the gauges 69 and 73. If desired, a pressure transducer (not shown) can be provided within the cavity 17 and connected through electric conductors (not shown) extending to the proximal extremity of the catheter where the pressure can be read on an appropriate instrument (not shown).

Figure 3:
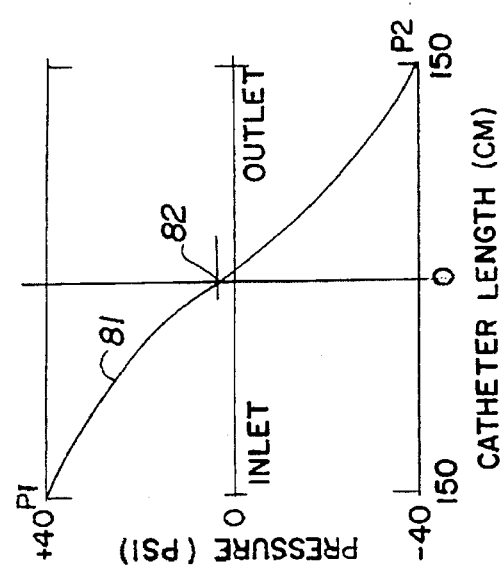
FIG. 3 is a graph showing the positive and negative pressure at the cooled tip is zero at or near the blood pressure range.
Figure 2:
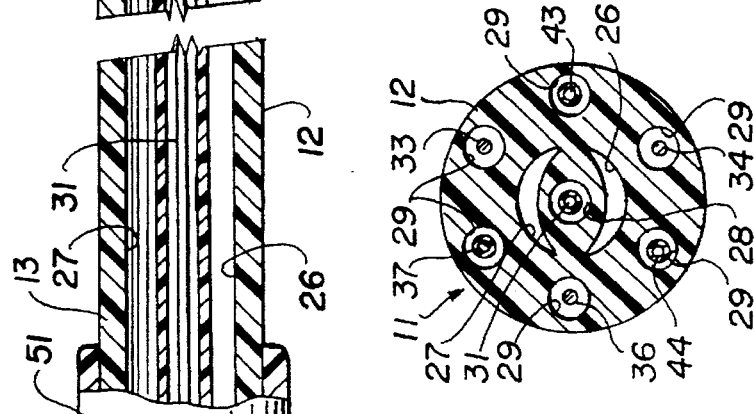
FIG. 2 is a cross-sectional view taken along line 2—2 of FIG. 1.

By maintaining the pressure of the saline solution in the cavity 17, at or near the pressure of the blood in which the distal extremity 14 of the catheter 11 is disposed, there is a minimal tendency for leakage of the saline solution from the cavity 17 of the catheter 1. This is readily accomplished even though there is a blood pressure change from systolic to diastolic as the heart is pumping blood during the time that an ablation procedure is being performed. This is illustrated in FIG. 3 in which the blood pressure range between systolic and diastolic is shown as ranging from 60–200 millimeters of mercury as approximately 2 psi. The pressure changes of the cooled liquid in the lumens 27 and 28 is shown by the curve 81. The inlet pressure provided by the pump 66 is P1 as shown in FIG. 3. The pressure drops in the lumen 27 because of losses in the lumen. Because of the negative pressure p2 created by pump 71 at the outlet of the lumen 28, the pressure continues to drop. By appropriate adjustment of the pressures P1 and P2 to overcome lumen losses, the pressure in the cavity 17 of the tip electrode 16 can be adjusted so that it approximates the pressure of the blood in the chamber in which the tip 16 is disposed. This is represented by the curve 81 in FIG. 3 which crosses through the blood pressure range at the tip lumen as indicated at 82. A typical example is shows in FIG. 3 with a catheter 150 centimeters in length and having lumens 0.010" in diameter. A pressure for the cooling liquid at the tip was obtained utilizing a positive input pressure P1 of 40 psi and a negative-outlet pressure P2 of negative 40 psi.

It has been found that with a catheter of the present invention utilizing the method of the present invention it has been possible to achieve lesions of the desired depth of ½ to 1 millimeter and a similar width in the myocardium utilizing 5 to 50 watts of power.

In addition to controlling the pressure in the cavity 17, it still may be desirable to measure the temperature of the tip electrode 16. This can be accomplished by mounting a thermocouple 83 in close proximity to the tip 16 and by bringing out leads 84 from the thermocouple through an additional lumen (not shown) in the elongate member 12 and bringing the leads out to the proximal extremity and connecting them into instrumentation 85 coupled to the controller 76 to make the temperature reading and control the application of RF energy by the controller in accordance with the temperature reading. This will provide still additional input to the physician or surgeon performing the ablation procedure to ensure that the cooling is adequate and to see that excessive temperature is not reached during the ablation procedure.

In order to enhance the cooling of a hollow tip electrode 16 such as shown in FIG. 1, there is provided a modified tip electrode 86 in FIGS. 4 and 5. As shown therein, the electrode 86 which can be formed of a suitable conducting material is provided with a plurality of radially extending fins 87 which extend inwardly from the cylindrical wall 88 of the tip 86 and extend to the distal extremity of the tip as shown particularly in FIG. 4. The fins 87 terminate short of the longitudinal axis of the tip 86 to provide a cylindrical space 89 at the extremities of the fins 87. Thus, it can be seen as a cooled saline solution enters the tip 86 in the same manner as saline solution is introduced in the tip 16, the additional cooling surfaces of the fins 87 will cause additional heat transfer from the electrode 86 to the cooling electrode 86. This increased heat transfer from the tip to the cooled saline solution makes possible less flow of the cooled saline solution or the application of additional RF energy to the electrode during the ablation procedure which is being accomplished.

Another embodiment of the catheter for radio frequency ablation with a cooled electrode is shown in FIGS. 6–8. The catheter 91 consists of a flexible elongate member having proximal and distal extremities 13 and 14. The catheter 92 is of a suitable length as for example 150 centimeters and is provided with a flow passage 96. The distal extremity 94 is provided with a portion 92a of reduced diameter and a flow passage 97 therein which is in communication with the passage 96. The flexible elongate member 92 is also provided with the tapered portion 92b which forms a transition between the distal extremity 94 and the portion 92a of reduced diameter. The passage 97 is in communication with chamber 98 provided within a cup-shaped electrode 99 formed of a suitable conductive material such as silver which serves as a hollow tip conducting electrode. The cup-shaped electrode 99 has a proximal extremity 101 secured to the distal extremity 94 of the flexible elongate member 92 by suitable means such as an adhesive 102. The electrode 99 is provided with a hemispherical distal extremity 103 having a plurality of spaced-apart holes 106. In addition, the electrode 99 is provided with a pair of moon-shaped spaced-apart slots 107 and 108 as shown in FIGS. 7 and 8 which are inclined proximally to extend at an angle of approximately 45° with respect to the axis of the tip 99.

Means is provided for supplying a cooling liquid to the chamber 98, in the electrode 99 and consists of a vessel 111 having a cooled saline solution therein which can be replenished when desired. Means is provided for supplying the cooled saline solution from the tank or vessel 111 to the passage 96 of the catheter 11 and consists of an inlet pipe 112 which is connected to a pump 113. The pump 113 is connected through a stop cock 114 which is provided with a handle 116 for moving the same between open and closed positions to provide a three-way valve. The stop cock 114 is connected to flexible piping 117 connected to a fitting 118 secured to the proximal extremity 93 of the flexible elongate member 92.

In addition means is provided for supplying radio frequency energy to the tip 99 and consists of a radio frequency power supply 121 which provided with a power supply cord 122 connected to a connector 123. The connector 123 is connected to another connector 124 which is connected to a cord 126 that is connected into the fitting 118. The cord is conducted by an insulated wire 127 to the electrode 99 by solder 128.

Operation and use of the cooled tip catheter as shown in FIGS. 6 through 8 may now be described as follows. The one-way pump 113 serves to pump the cooled saline solution from the vessel 111 and supplies it under pressure through the passage 96, through the passage 97 and into the chamber 98. The cooled saline solution rather than being recirculated as in the embodiment shown in FIG. 1 is discharged from the electrode 99 by jets 131 of cooling liquid passing from the electrode 99 after the cooled liquid has come into contact with the electrode. Thus, it can be seen that when the tip 99 is in contact with the wall of the heart, the jets will permeate the interface between the tip 99 and the wall of the heart to produce additional cooling. Although the cooled saline solution may have been warmed slightly by the temperature of the tip 99, the jets 131 will still be cooler than the surrounding blood and therefore provide additional cooling at the interface to help prevent coagulation of the blood at the interface between the tip 99 and the wall of the heart. In addition to the jets 131, they will be additional jets indicated by the arrows 132 directed proximally from the slots 107 and 108 which will create a force that urges the electrode 99 into contact with the wall of the heart. In other words, jets 132 will create a counter force to the jets 131 to cause the electrode tip 99 to remain in contact with the wall of the heart.

From the foregoing it can be seen that for a given size catheter it is possible to provide a much larger lumen extending to the distal extremity 94 because only one lumen is required for the one-way flow of the cooled saline solution. This increased flow rate of the saline solution makes it possible to increase the radio frequency power delivered to the tip electrode 99 to make it possible to create larger lesions in the wall of the heart when desired. The introduction of the saline solution into the blood is not objectional because it is already done in a number of other medical procedures.

The three-way valve or stop cock 114 provided makes it possible to drain any air out of the catheter 91 to insure that no air bubbles will be pumped by the pump 113 when pumping the cooled saline solution into the catheter 91. As soon as the air has been exhausted from the system, the handle 116 can be turned so that the cooled saline solution is supplied to the flow passage 96.

By providing the catheter 91 with a cooled ablation electrode which can accommodate more radio frequency energy, it is possible to perform ablation procedures other than in the heart. For example, it can be utilized to treat certain tumors. It also can be utilized in electrocautery and electrosurgery which may make it possible to leave the surface intact while treating the tissue underlying the surface without damaging the bonding of the surface to the tissue. Thus, in treating an organ through a vein or arterial wall, it is possible to do this while still preserving the vein or arterial wall without damaging the lining of the wall. This can be readily accomplished by the cooled tip with the saline solution flowing from the same as shown in FIG. 4 to prevent damage to the wall. Such procedures are particularly applicable for gall bladder, urology, and gynecology.

In order to prevent blood from entering into the holes 106 and the slots 107 and 108 during the introduction of the catheter 91 into the vessel of the patient, it may be desirable to have the cooled saline solution under a slight positive pressure as the catheter 91 is introduced into the passage 96 so that saline solution will be flowing out of the holes 106 and the slots 107 and 108. Another alternative would be to apply the cooling saline solution through the passage 96 before RF energy is applied to the tip 99. This will help to ensure that any blood within the catheter will be forced out into the blood pool in which the catheter is disposed. This will prevent blood from becoming coagulated within the small holes 106 or the slots 107 and 108 when RF energy is applied and the tip electrode 99 is heated.

Another embodiment of a catheter incorporating the present invention making it more difficult for the blood to enter into the interior of the catheter is shown in FIGS. 9–10. As shown therein, the catheter 136 consists of a flexible elongate tubular member 137 which is provided with a flow passage 138. A tip electrode 141 formed of a suitable conducting material is adhered to the distal extremity 142 of the tubular member 137 by suitable means such as adhesive 143. A tubular insert 144 of a suitable material such as plastic is provided with a flared proximal extremity 144a secured to the interior wall of the flexible elongate member 137 by suitable means such as an adhesive 146. As can be seen in FIG. 9, the tubular insert 144 is provided with a distal extremity 147 which terminates short of the hemispherical portion of the tip electrode 141 to provide a space or chamber 148 within the electrode 141. The tubular insert 144 is provided with a flow passage 149 which opens through the distal extremity 147 and which is in communication with the chamber 148. The flow passage 149 is also in communication with the flow passage 138 in the flexible elongate member 137. A pair of diametrically opposed holes 151 are provided in the distal extremity 142 of the flexible elongate tubular member 137. Valve means in the form of a cylindrical valve sleeve 153 formed of a suitable elastomeric material is disposed in recess 154 provided in the distal extremity 142 of the flexible elongate tubular member 137. The valve sleeve 153 is provided with annular reinforcing ribs which extend circumferentially around the sleeve 153. Slits 157 extending longitudinally of the tubular insert 144 are provided which overlie the holes 151 and serve to form leaflets 153a and 153b yieldably retained in a sealed position to close the slit 157.

It can be seen that when a cooled saline solution is introduced through the passage 138 in the catheter 136, the solution will pass through the passage 149 as indicated by the arrows 157 into the chamber 148 where it will cool the tip 141. After its cooling function has been performed, the slightly heated cooled liquid will pass proximally as indicated by the arrows 157 and be discharged into the blood pool under positive pressure through the holes 151 and through the slits 157 by urging outwardly the leaflets 153a and 153b provided in the valve sleeve 153. This will permit additional cooled saline solution to be introduced into the tip electrode 141 to continue cooling of the electrode. Thus, it can be seen that such a valve sleeve 153 permits the use of a cooled saline solution while preventing blood surrounding the catheter 136 from entering into the interior of the catheter when a saline solution is not being supplied to the catheter 136.

In certain applications, it may be possible to forego the use of active cooling as for example as by the providing of the cooled saline solution as hereinbefore described and to rely upon passive cooling for the tip of the catheter while it is being utilized for RF ablation. Such a catheter 171 is shown in FIGS. 11 and 12 and consists of a flexible elongate tubular member 172 formed of the plastic hereinbefore described which is provided with a flow passage 173 extending therethrough. The tubular member 172 is connected to a cylindrical metal sleeve 176 formed of a suitable conducting material such as silver. The sleeve can have a suitable length as for example from 2 to 5 centimeters. The sleeve 176 is provided with a bore 177 extending therethrough. The other end of the sleeve 176 is connected to another tubular member 179 formed of a suitable insulating material such as plastic. The tubular member 179 is provided with a large central lumen 181 and a plurality of additional lumens 181 through 187 which are spacial circumferentially around the lumen 181. The lumens 182, 184, and 185 have elements 191, 192, and 193 extending therethrough which are connected to the distal extremity of the tubular member 179. These elements 191, 192 and 193 are formed of a material such as Nitinol having a negative coefficient of expansion. A ground return conductor 194 is provided in the lumen 183. A conductor 196 is provided in the lumen 186 and is connected to a hemispherical tip electrode 198 formed of a conducting material and secured to the distal extremity of the tubular member 179 by suitable means such as an adhesive (not shown).

Passive heat conduction means 201 is provided within the distal extremity of the catheter 171 and consists of a suitable fibrous material such cotton fibers which have been impregnated with a heat absorbing fluid as for example water or a saline solution. This heat conducting material 201 extends from the distal extremity of the tubular member 172 through the passage 177 in the metal sleeve 176 and is in intimate contact with the metal sleeve 176. The material 201 also extends through the lumen 181 provided in the tubular member 179 and into the interior of the tip electrode 197. As can be seen from FIG. 11, the various conductors and elements hereinbefore described in the lumens 182 through 186 extend through the passive heat conducting material 201 and pass through an adhesive 206 then through the passage 173 to the proximal extremity of the catheter 181 where they are connected to appropriate controls of the type hereinbefore described.

In use of the catheter 171 as shown in FIGS. 11 and 12, the application of radio frequency energy to the electrode 197 heats the electrodes 176 and 197 will cause the liquid within the passive heat conducting means to heat up and to travel by convection towards the cooler region of the passive heat conductive material 201. This in turn will cause the cooler liquid to circulate and take its place. The liquid which has been heated will move through the wick-like heat conductive material 201 and will come into contact with the metal sleeve 176 which will cause cooling to occur by having heat pass therethrough into the blood passing the sleeve 176. The cooled liquid will then return to the tip to continue the convective flow as herein before described.

Additionally, if additional heat dissipation is desired, a construction such as that shown in FIG. 13 can be used. Radially extending heat conducting fins 211 of metal are either soldered on or formed integral with the sleeve 176 on the outer surface thereof. By providing the fins 211, additional heat dissipating surface area is provided which increases the capabilities for dissipating heat into the blood circulating around the sleeve 176 and the fins 211.

Figure 14:
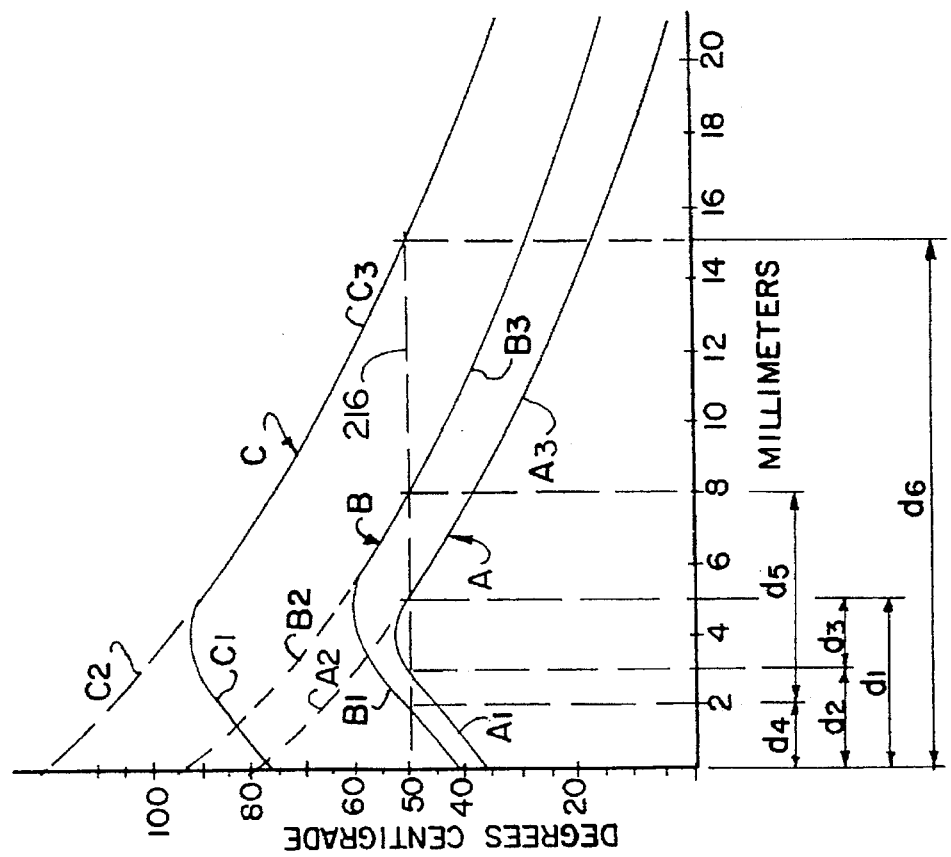
FIG. 14 is a graph showing the temperatures which are encountered in tissue during an ablation procedure.

The functioning of the catheters hereinbefore described in conjunction with ablation by the use of radio frequency energy can be more clearly understood by reference to FIG. 14. FIG. 14 is a graph which along the horizontal axis shows the depth of the lesion created during the ablation procedure in millimeters with respect to temperature in degrees centigrade as shown by the vertical axis of the graph. "0" on the graph is equivalent to the surface of the tip of the electrode which is in contact with the tissue. Going to the right of the graph as shown in FIG. 14, the depth into the tissue increases. Three curves A, B, and C are shown in the graph for three different power levels of radio frequency energy being delivered into the tissue. The temperature on the graph goes to 100° C. The 100° C. has been shown because it is considered to be an upper limit for temperature or slightly less than that because at approximately 90° C. blood begins to boil and coagulate on the electrode tip greatly increasing its impedance and comprising its ability to create lesions. Thus, it is desirable to have the temperature of the electrode or tip remain below 90° C. if possible. At 50° C. a line 216 has been shown on the graph because this is the temperature below which necrosis of the myocardial as well as connective tissue will cease.

Curve A shown in FIG. 14 is divided into three segments A1, A2, and A3. The broken line segment A2 represents a continuation of the exponential curve A3 when no cooling applied to the electrode. Thus it can be seen from the power level of 5 watts represented by the curve A that from the tip temperature of 80° C. shown at the commencement of the curve, the temperature decreases exponentially as the distance from the surface of the tissue increases. As shown, the curve A3 crosses the 50° C. necrosis boundary represented by the line 216 at a depth of 5 millimeters. The lesion created would have a depth of approximately 5 millimeters as represented by the distance d1. Further ablation would stop at this power level. If the tip electrode being supplied with the power level represented by the curve A is actively cooled in a manner hereinbefore described, the tip electrode temperature drops to a much lower level, as for example 35° C. as represented by the curve A1 at the tip of skin interface at 0 millimeters in distance. Since this temperature is below the necrosis temperature, ablation will not begin to occur until a distance of d2 at the point where the curve A2 crosses the necrosis line at 50° C., as for example a depth of 3 millimeters from the surface. Necrosis will occur at a depth from 3 millimeters to 5 millimeters as represented by the distance d3. Such a cooled ablation procedure is very advantageous because it permits necrosis to occur below the contact surface without destroying the contact surface and the tissue immediately underlying the same. This is particularly desirable in applications, for example in the heart, in which it is desired to ablate certain tissues to destroy sites circuits which are causing arrhythmias in the heart without destroying the surface lining of the heart.

The curve B represents what occurs with and without cooling of the electrode tip at a higher power level for example, 10 watts of radio frequency energy for causing $I^2 R$ heating inside the tissue. Segment B2 of curve B represents a continuation of the exponential curve of the Segment B3. As can be seen, the temperature at the tip-skin interface approaches 100° C. which is very objectionable because that is a temperature which boiling of the blood and coagulation of the blood on the electrode making its impedance high and comprising the ability to create lesions. By providing active cooling to the tip electrode, the curve B1 is generated which shows the temperature at the skin-tip interface drops to approximately 40° C. and causing necrosis to occur from the depth of two millimeters as represented by d4 and extending to a depth of approximately 8 millimeters where the curve B3 crosses the 50° C. necrosis line 216 as represented by d5. Thus it can be seen that it is possible to provide a much deeper and larger lesion using the higher power level without reaching an undesirable high temperature which could cause coagulation of the blood on the tip of the electrode. As shown, it is still possible to commence the formation at the lesion below the surface so that the surface need not be destroyed thus facilitating early recovery by the patient from a treatment in accordance with the present invention.

Curve C represents a still higher power level, as for example 40 watts in which the curve is represented by segments C1, C2, and C3. The broken line segment C2 which is a continuation of the exponential curve C3 shows that the temperature at the electrode skin interface far exceeds the 100° C. and would be unusable except with active cooling provided in accordance with the present invention. With active cooling, it can be seen that the temperature at the skin electrode interface approaches 80° C. and gradually increases and approaches near 95° C. and then drops off exponentially to cross the necrosis line 216 at a distance of 15 millimeters from the surface of the skin represented by the distance d6. In view of the fact that the starting temperature is above the 50° C. necrosis line 216, necrosis will occur from the surface of the skin to the 15 millimeter depth to provide large and deep lesions.

Figure 18:
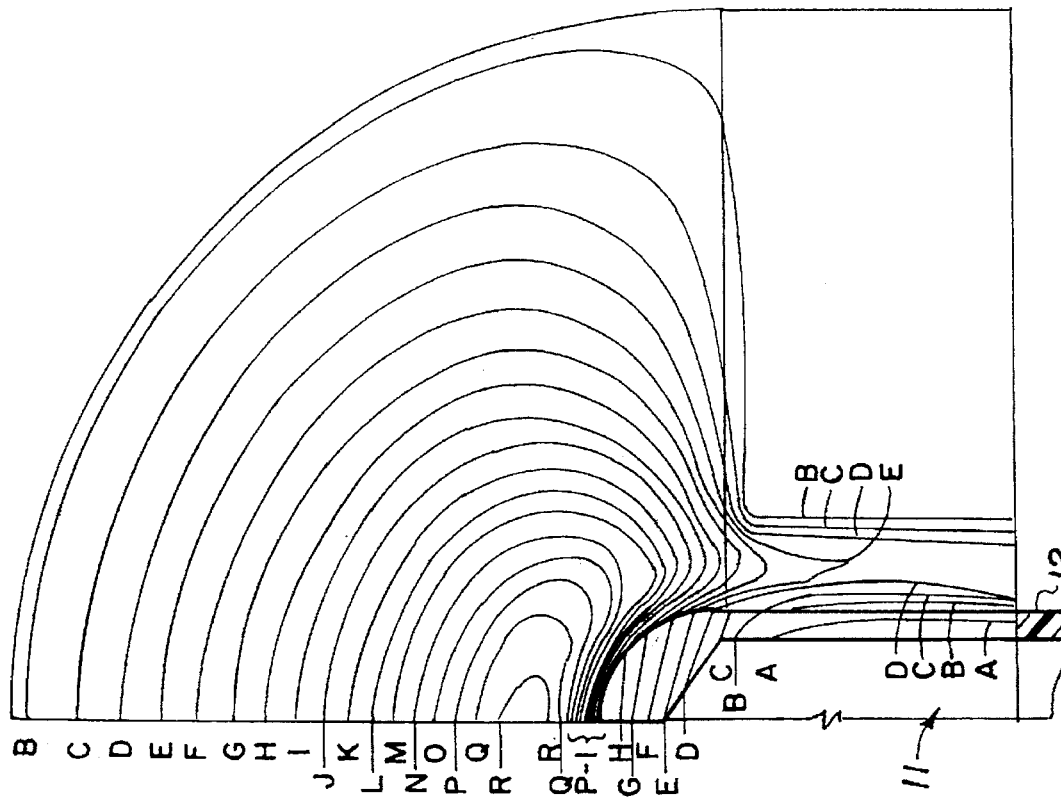
FIGS. 15—18 show graphs showing isothermal curves comparing cooled and uncooled electrodes and the effect on tissue during ablation.
Figure 17:
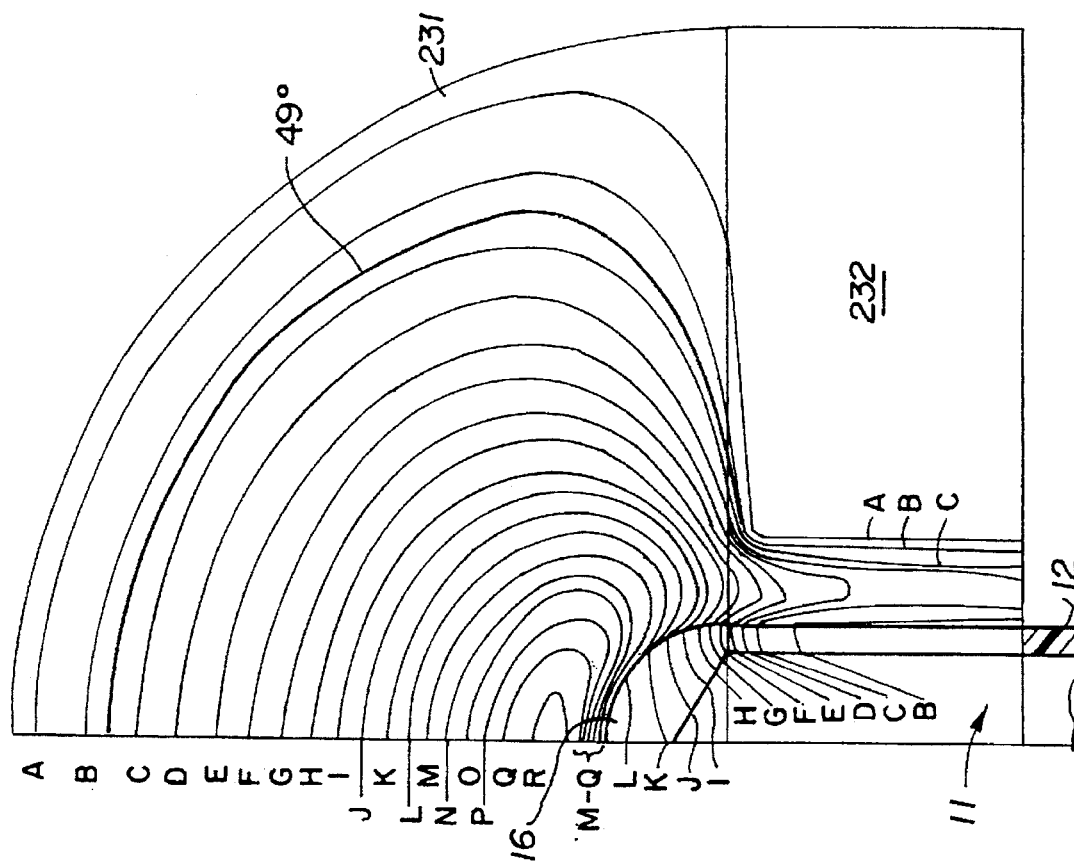
Figure 16:
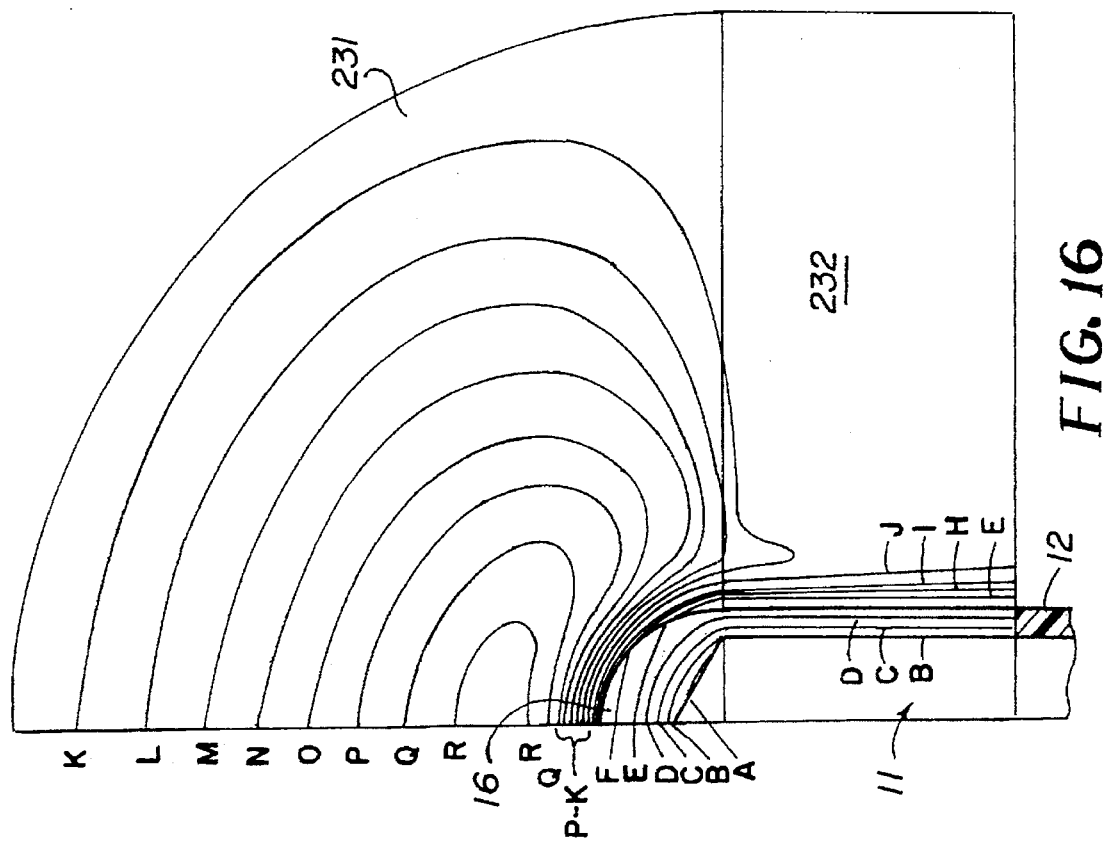

The results which are reflected in the graph in FIG. 14 are also reinforced by the thermal contour maps shown in FIGS. 16–18, which show for cooled electrodes that the higher temperatures are only reached at depths which are distant from the electrode skin interface.

Figure 15:
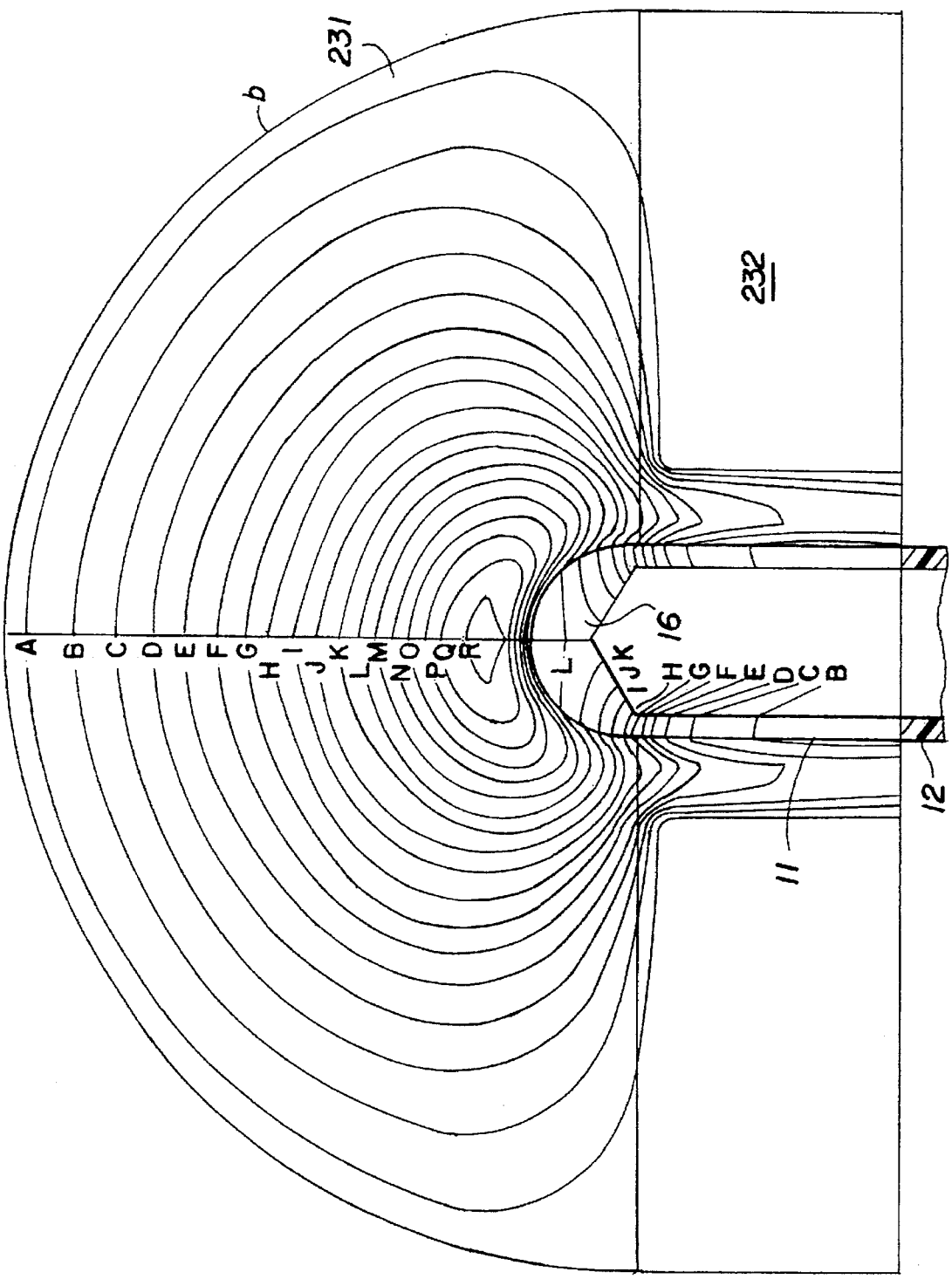

FIGS. 15, 16, 17 and 18 are graphs which were derived from a computer simulation utilizing the finite element analysis program ANSYS. The graphs show computer generated isothermal curves showing the temperatures which are reached at the electrode 16 at the tip of the distal extremity of the flexible elongate member 12 of the catheter 11 and at different depths in the tissue from the electrode-tissue interference for different conditions. FIG. 15 represents the situation where 10 watts of power are applied to the electrode 16 with no chilling. FIG. 16 is for the same 10 watts of power applied to the electrode 16 with cooling in the form of 20 ccs per minute of a saline solution delivered to the electrode at 5° C. FIG. 17 is for a situation where 40 watts of power is applied to the electrode 16 without chilling whereas FIG. 18 is for the situation where the same 40 watts of power are applied to the electrode with cooling being applied to the electrode by 20 ccs per minute of a saline solution at a temperature of 5° C. The graphs or diagrams shown in FIGS. 16-18 only represent one-half of the temperature profiles or contours extending radially away from the longitudinal axis of the distal extremity of the flexible elongate member 12 of the electrode tip 16.

In the graphs shown in FIGS. 15-18 it is assumed that the electrode tip 16 is in contact with tissue such as in contact with the myocardium of the human heart. The myocardium is identified as 231 with the blood in the heart being identified as 232. As can be seen from the graphs in FIGS. 15 through 18 the isothermal curves are identified by letters of the alphabet. The isothermal curves shown in FIG. 15 represent the following temperatures at degrees centigrade for an electrode 16 without cooling.

A=37.811° centigrade
B=39.433° centigrade
C=41.056° centigrade
D=42.678° centigrade
E=44.300° centigrade
F=45.923° centigrade
G=47.545° centigrade
H=49.167° centigrade
I=50.789° centigrade
J=52.412° centigrade
K=54.034° centigrade
L=55.656° centigrade
M=57.279° centigrade
N=58.901° centigrade
O=60.523° centigrade
P=62.145° centigrade
R=65.390° centigrade The curve H identified above that represents a temperature of approximately 50° C. which is a temperature at which permanent necrosis occurs in the tissue as for example in the myocardium. In other words, irreversible damage occurs at temperatures higher than this temperature. Below that temperature the edema is temporary and typically reverses. The temperatures represented by the curves I, J, K, L through R represent temperatures above 50° at which necrosis would take place. Thus, because of the temperatures reached, there would be necrosis occurring from the tip 16 out to a distance or depth represented by the curve H in FIG. 15.

In contrast, by utilizing cooling of the electrode 16 as shown in FIG. 16, the isothermal curves have the following temperatures.

A=19.518° centigrade.
B=21.425° centigrade
C=23.333° centigrade
D=25.240° centigrade
E=27.148° centigrade
F=29.055° centigrade
G=30.963° centigrade
H=32.870° centigrade
I=34.778° centigrade
J=36.685° centigrade
K=38.593° centigrade
L=40.500° centigrade
M=42.408° centigrade
N=44.315° centigrade
O=47.228° centigrade
P=48.130° centigrade
R=51.945° centigrade From the isothermal curves it can be seen that the 50° C. isothermal curve is spaced from the electrode tip that the temperature only begins to exceed 49°-50° C. in the vicinity of the isotherm curve R. Thus it can be seen that a portion of the myocardium immediately adjacent to the tip is saved. In other words, necrosis does not appear in the first portion of the myocardium because of the cooled tip necrosis does not occur until a certain distance as for example 1 or 2 millimeters below the surface of the myocardium as presented by the curves P and R. Thus it can be seen that the cooling of the ablation tip serves to preserve the surface of the myocardium. At the same time the cooled tip serves to prevent coagulation of the blood which could inhibit power delivery into the myocardium.

In the graph shown in FIG. 17, the isothermal curves have the following temperatures.

A=40.160° centigrade
B=46.479° centigrade
C=52.798° centigrade
D=59.117° centigrade
E=65.436° centigrade
F=71.756° centigrade
G=78.075° centigrade
H=84.394° centigrade
I=90.713° centigrade
J=97.032° centigrade
K=103.352° centigrade
L=109.671° centigrade
M=1115.990° centigrade
N=122.309° centigrade
O=128.629° centigrade
P=134.943° centigrade
R=147.586° centigrade Here it can be seen that relatively high temperatures are reached which are substantially above the 100° C. at which blood coagulates on the electrode surface. Although a 49° C. isothermal is not shown in FIG. 17, it would be between isothermal curves B and C. Thus, but for the coagulation of the blood at the electrode tip necrosis should occur to a depth represented by a curve between the curves C and D. This is theoretical only because with temperatures so high blood coagulation would occur on the tip and greatly interfere with the transfer of power from the tip to the tissue in the myocardium.

In the graph shown in FIG. 18, the isothermal curves have the following temperatures.

A=32.980° centigrade
B=38.589° centigrade
C=44.197° centigrade

D=49.806° centigrade
E=55.415° centigrade
F=61.024° centigrade
G=66.633° centigrade
H=72.242° centigrade
I=77.851° centigrade
J=83.460° centigrade
K=89.069° centigrade
L=94.678° centigrade
M=100.386° centigrade
N=105.895° centigrade
O=111.504° centigrade
P=117.113° centigrade
R=128.331° centigrade From these curves it can be seen that curve D is an isothermal curve representing the region at which necrosis would stop. From the isothermal curves in FIG. 18 it can be seen that the temperatures at the surface of the electrode are substantially below 100° and therefore coagulation of blood is inhibited from taking place. Thus it is possible to achieve relatively deep and wide lesions utilizing a cooled ablation electrode which heretofore was not possible to achieve without cooling. Without the use of cooling for the ablation tip electrode, the amount of power which can be supplied to the tip electrode is greatly reduced because otherwise the tip electrode temperature rises very rapidly causing coagulation of blood on the tip which prevents or at least inhibits the transfer of power from the electrode to the tissue in contact with the electrode.

From the foregoing it can be seen that the provision of a cooled ablation electrode has a number of unexpected results. The use of the cooled electrode makes it possible to create necroses well below the surface being contacted by the electrode. This is particularly desirable for treating arrhythmias which are created by sub-endocardial arrhythmogenic foci, this makes it possible to spare the endocardium. Thus it is possible to achieve lesions which are several millimeters below the tissue surface making it possible to treat tumor cells which underlie the skin surface without damaging or breaking the skin surface. This is a great aid in preventing potential infections in a wound. It also facilitates faster healing for the patient around the necrosis which has been created. Thus in accordance with the present invention, it is possible to provide very small lesions for example 2 and 3 millimeter diameter lesions in the middle of the myocardium. By the appropriate application of power and the appropriate removal of heat from the electrode it is possible to achieve lesions at any desired depth in tissue without the surface being damaged by the electrode.

Although the present invention is primarily been described in connection with ablation of the heart, it should be appreciated that also has other applications as for example electrosurgery. It also can be used for treating tumors underlying the skin as for example breast cancer and prostatic cancer.

In view of the foregoing, it can be seen that there has been provided a catheter which is particularly suitable for radio frequency ablation that is provided with a cooled electrode and a method for using the same which makes possible to ablate the myocardium of the heart without creating undue heating of the blood in the vicinity of the region where the ablation is being performed and without causing blood degradation. This can be accomplished by the use of a cooled saline solution which is maintained at a pressure at the tip of the catheter which is substantially equal to the pressure of the blood at the tip.

What is claimed is:

1. A method for creating a lesion in tissue having blood therein and having a surface by the use of an impervious metal conducting electrode having a chamber therein comprising bringing the electrode into contact with the surface of the tissue to form an electrode-surface interface, supplying radio frequency energy at a predetermined power level in excess of 10 watts to the inpervious metal conducting electrode to cause heating of the tissue in the vicinity of the surface contacted by the impervious metal conducting electrode, cooling the impervious metal conducting electrode with a cooling liquid delivered into the chamber so that the temperature in the tissue does not reach a temperature in excess of approximately 95° C. and thereby inhibiting coagulation of blood on the impervious metal conducting electrode and making possible the formation of a wide and deep lesion in the tissue.

2. A method for controlling the temperature of an energy delivering electrode disposed on an ablation catheter for forming a lesion in tissue in an internal organ having blood therein comprising providing an ablation catheter in the form of a thin, flexible elongate member having disposed at a distal portion thereof at least one imprevious energy delivering electrode having a chamber therein, the catheter having a liquid delivering lumen associated therewith in communication with the chamber and being adapted for intravascular delivery to an internal organ and being in electrical communication with a radio frequency power supply, intravascularly delivering the catheter to an internal organ, delivering radio frequency energy in excess of 10 watts of power from the power supply through the catheter to the impervious energy delivering electrode and into the tissue, selectively delivering a cooling liquid through the lumen of the cathether into the chamber at a desired flow rate and adjusting the flow rate of the cooling liquid through the lumen of the catheter so that a wide and deep lesion is formed in the tissue while inhibiting the coagulation of blood on the electrode.

3. A method as in claim 2 wherein the step of selectively delivering cooling liquid further comprises the step of allowing the cooling liquid to exit the catheter at a distal portion thereof.

4. A method as in claim 3 wherein [the flow rate is adjusted by a ]pump means is provided for supplying the cooling liquid and further comprising the step of controlling the pump means to adjust the flow rate of the cooling liquid.

5. A method for performing an ablation in the myocardium of a heart by utilizing a catheter having a distal extremity with an impervious conductive electrode having a chamber therein mounted thereon comprising introducing the catheter into the heart so that the electrode is in contact with the myocardium, supplying radio frequency energy to the electrode at a power level in excess of 10 watts and supplying a cooling liquid to the chamber of the electrode for cooling the electrode during the time that the radio frequency energy is being supplied to the electrode and withdrawing the cooling liquid after it has cooled the electrode to make possible the formation of a wide and deep lesion in the myocardium while inhibiting the coagulation of blood on the conductive electrode.

6. A method as in claim 5 further comprising adjusting the power level so that it is between 10 and 50 watts.

7. A method as in claim 6 further comprising sensing the temperature of the tissue of the myocardium and adjusting the power level in accordance with the sensed temperature.

* * * * *